United States Patent
Vanleeuwen et al.

(10) Patent No.: US 10,195,042 B2
(45) Date of Patent: Feb. 5, 2019

(54) BALLOON IMPLANT DEVICE

(71) Applicant: MicroAire Surgical Instruments LLC, Charlottesville, VA (US)

(72) Inventors: Ryan Vanleeuwen, Ruckersville, VA (US); Shannon Vaughn, Stanardsville, VA (US); Thomas Weisel, Ventura, CA (US)

(73) Assignee: Microaire Surgical Instruments LLC, Charlottesville, VA (US)

( * ) Notice: Subject to any disclaimer, the term of this patent is extended or adjusted under 35 U.S.C. 154(b) by 0 days.

(21) Appl. No.: 15/727,437

(22) Filed: Oct. 6, 2017

(65) Prior Publication Data

US 2018/0028326 A1    Feb. 1, 2018

Related U.S. Application Data

(60) Division of application No. 15/162,148, filed on May 23, 2016, now Pat. No. 9,949,838, which is a
(Continued)

(51) Int. Cl.
*A61F 2/40* (2006.01)
*A61F 2/30* (2006.01)
(Continued)

(52) U.S. Cl.
CPC ............ *A61F 2/40* (2013.01); *A61B 17/1778* (2016.11); *A61F 2/30756* (2013.01);
(Continued)

(58) Field of Classification Search
CPC ........ A61F 2/40; A61F 2/4225; A61F 2/4241; A61F 2/4405; A61F 2/44; A61F 2/441;
(Continued)

(56) References Cited

U.S. PATENT DOCUMENTS

| 3,875,595 A * | 4/1975 | Froning ................ A61F 2/441 623/17.12 |
| 4,772,287 A | 9/1988 | Ray et al. |

(Continued)

FOREIGN PATENT DOCUMENTS

| WO | 2008111073 A1 | 9/2008 |
| WO | 2009023250 A1 | 2/2009 |

(Continued)

*Primary Examiner* — Alvin Stewart
(74) *Attorney, Agent, or Firm* — Suiter Swantz pc llo

(57) ABSTRACT

A shoulder implant device includes one or more fixation features including an acromial intrusion element and an inflatable humeral balloon portion that receives a fluid through the acromial intrusion element. The intrusion element comprises a valve that can receive multiple needle sticks to add or remove fluid to or from the inflatable humeral balloon. The device is implanted in a subacromial space such that the one or more fixation features at least secure the device to the acromion and the inflatable balloon portion rests against the proximal end of the corresponding humerus. Fluid in the balloon portion maintains separation of the acromion and the humerus to reduce or prevent impingement.

5 Claims, 20 Drawing Sheets

Related U.S. Application Data continuation of application No. 14/213,009, filed on Mar. 14, 2014, now Pat. No. 9,345,577.

(60) Provisional application No. 61/786,263, filed on Mar. 14, 2013.

(51) Int. Cl.
*A61B 17/17* (2006.01)
*A61B 17/84* (2006.01)
*A61B 17/04* (2006.01)
*A61F 2/46* (2006.01)

(52) U.S. Cl.
CPC ..... *A61B 17/842* (2013.01); *A61B 2017/0414* (2013.01); *A61F 2002/30578* (2013.01); *A61F 2002/30581* (2013.01); *A61F 2002/30878* (2013.01); *A61F 2002/4088* (2013.01); *A61F 2002/4677* (2013.01); *A61F 2002/4687* (2013.01); *A61F 2220/0008* (2013.01); *A61F 2220/0075* (2013.01); *A61F 2250/0003* (2013.01)

(58) Field of Classification Search
CPC ........ A61F 2/38; A61F 2/389; A61F 2/30756; A61F 2002/30121; A61F 2/442; A61F 2/2433; A61F 2002/30019; A61F 2002/30581; A61F 2002/30584; A61F 2002/30589; A61F 2002/501; A61F 2002/5012; A61F 2002/4088; A61F 2002/4092; A61B 17/1739; A61B 17/1684; A61B 17/1778; A61B 17/7097; A61B 17/8855; A61B 17/8805
See application file for complete search history.

(56) References Cited

U.S. PATENT DOCUMENTS

| | | | |
|---|---|---|---|
| 4,932,969 A | 6/1990 | Frey et al. | |
| 4,969,888 A | 11/1990 | Scholten et al. | |
| 5,496,318 A | 3/1996 | Howland et al. | |
| 5,549,679 A | 8/1996 | Kuslich | |
| 5,674,295 A | 10/1997 | Ray et al. | |
| 5,702,454 A | 12/1997 | Baumgartner | |
| 5,824,093 A | 10/1998 | Ray et al. | |
| 5,888,220 A | 3/1999 | Felt et al. | |
| 5,944,757 A | 8/1999 | Grammont | |
| 5,997,582 A | 12/1999 | Weiss | |
| 6,022,376 A | 2/2000 | Assell et al. | |
| 6,066,154 A | 5/2000 | Reiley et al. | |
| 6,110,211 A * | 8/2000 | Weiss | A61F 2/30756 606/89 |
| 6,248,131 B1 | 6/2001 | Felt et al. | |
| 6,402,784 B1 | 6/2002 | Wardlaw | |
| 6,419,704 B1 | 7/2002 | Ferree | |
| 6,423,083 B2 | 7/2002 | Reiley et al. | |
| 6,591,838 B2 | 7/2003 | Durgin | |
| 6,602,291 B1 | 8/2003 | Ray et al. | |
| 6,626,944 B1 | 9/2003 | Taylor | |
| 6,733,531 B1 | 5/2004 | Trieu | |
| 6,733,533 B1 | 5/2004 | Lozier | |
| 6,761,720 B1 | 7/2004 | Senegas | |
| 6,764,514 B1 | 7/2004 | Li et al. | |
| 6,946,000 B2 | 9/2005 | Senegas et al. | |
| 6,966,931 B2 | 11/2005 | Huang | |
| 7,156,877 B2 | 1/2007 | Lotz et al. | |
| 7,244,273 B2 | 7/2007 | Pedersen et al. | |
| 7,465,318 B2 | 12/2008 | Sennett et al. | |
| 7,491,236 B2 | 2/2009 | Cragg et al. | |
| 7,645,301 B2 * | 1/2010 | Hudgins | A61F 2/441 623/17.11 |
| 7,744,630 B2 | 6/2010 | Lancial | |
| 7,776,073 B2 | 8/2010 | Serhan et al. | |
| 7,887,586 B2 | 2/2011 | Linares | |
| 7,972,380 B2 | 7/2011 | Linares | |
| 8,123,808 B2 * | 2/2012 | Dewey | A61F 2/44 623/17.12 |
| 8,226,719 B2 | 7/2012 | Melsheimer et al. | |
| 8,282,681 B2 | 10/2012 | McLeod et al. | |
| 8,292,955 B2 * | 10/2012 | Robinson | A61F 2/4606 623/14.12 |
| 8,377,135 B1 | 2/2013 | McLeod et al. | |
| 8,435,301 B2 * | 5/2013 | Gerber | A61F 2/441 623/17.16 |
| 8,551,172 B2 * | 10/2013 | Park | A61F 2/441 623/17.12 |
| 8,636,803 B2 * | 1/2014 | Hibri | A61F 2/441 623/17.12 |
| 8,696,751 B2 * | 4/2014 | Ashley | A61F 2/442 623/17.16 |
| 8,771,363 B2 | 7/2014 | Grotz | |
| 8,894,713 B2 * | 11/2014 | Shohat | A61F 2/4081 606/90 |
| 8,900,304 B1 | 12/2014 | Alobaid | |
| 8,986,311 B2 | 3/2015 | Boudreault et al. | |
| 9,066,802 B2 | 6/2015 | Mansmann | |
| 9,132,015 B2 | 9/2015 | Bromer | |
| 9,345,577 B2 * | 5/2016 | Vanleeuwen | A61F 2/30756 |
| 9,949,838 B2 * | 4/2018 | Vanleeuwen | A61F 2/30756 |
| 2001/0004710 A1 * | 6/2001 | Felt | A61B 17/7097 623/17.12 |
| 2002/0147497 A1 | 10/2002 | Belef et al. | |
| 2003/0036797 A1 | 2/2003 | Malaviya et al. | |
| 2003/0144738 A1 | 7/2003 | Rogalski | |
| 2004/0024460 A1 | 2/2004 | Ferree | |
| 2004/0038874 A1 | 2/2004 | Omoigui | |
| 2004/0186576 A1 | 9/2004 | Biscup et al. | |
| 2004/0249463 A1 * | 12/2004 | Bindseil | A61F 2/28 623/17.16 |
| 2004/0260396 A1 | 12/2004 | Ferree et al. | |
| 2004/0267375 A1 | 12/2004 | Friedrichs | |
| 2005/0043808 A1 * | 2/2005 | Felt | A61B 17/1739 623/20.14 |
| 2005/0090901 A1 | 4/2005 | Studer | |
| 2005/0154469 A1 | 7/2005 | Novelli | |
| 2005/0245938 A1 * | 11/2005 | Kochan | A61B 17/7097 606/92 |
| 2005/0251259 A1 | 11/2005 | Suddaby | |
| 2006/0241766 A1 * | 10/2006 | Felton | A61F 2/4425 623/17.12 |
| 2007/0038292 A1 | 2/2007 | Danielpour | |
| 2007/0078477 A1 * | 4/2007 | Heneveld, Sr. | A61B 17/0218 606/191 |
| 2007/0179625 A1 | 8/2007 | Ekholm et al. | |
| 2007/0198022 A1 | 8/2007 | Lang et al. | |
| 2007/0276491 A1 | 11/2007 | Ahrens et al. | |
| 2008/0027470 A1 * | 1/2008 | Hart | A61K 38/1858 606/151 |
| 2008/0033471 A1 * | 2/2008 | Paz | A61B 17/0218 606/190 |
| 2008/0139876 A1 | 6/2008 | Kim | |
| 2008/0269897 A1 * | 10/2008 | Joshi | A61F 2/4405 623/17.11 |
| 2008/0305145 A1 * | 12/2008 | Shelby | A61F 2/4644 424/423 |
| 2009/0048683 A1 * | 2/2009 | Morris | A61B 17/56 623/23.48 |
| 2009/0076605 A1 | 3/2009 | Linares | |
| 2009/0112326 A1 * | 4/2009 | Lehuec | A61B 17/7062 623/17.16 |
| 2009/0187252 A1 * | 7/2009 | Howald | A61F 2/4603 623/22.15 |
| 2009/0312807 A1 * | 12/2009 | Boudreault | A61B 17/025 606/86 R |
| 2010/0010114 A1 | 1/2010 | Myung et al. | |
| 2010/0023126 A1 | 1/2010 | Grotz | |
| 2010/0023127 A1 * | 1/2010 | Shohat | A61B 17/562 623/14.12 |
| 2010/0106252 A1 | 4/2010 | Kohm et al. | |
| 2010/0125341 A1 | 5/2010 | Frauens | |

(56) References Cited

U.S. PATENT DOCUMENTS

| | | |
|---|---|---|
| 2010/0160917 A1 | 6/2010 | Fitz et al. |
| 2010/0191332 A1* | 7/2010 | Euteneuer ............ A61F 2/0063 |
| | | 623/13.15 |
| 2010/0249855 A1 | 9/2010 | Bless |
| 2011/0066192 A1 | 3/2011 | Frasier et al. |
| 2011/0178603 A1 | 7/2011 | Long |
| 2011/0295370 A1* | 12/2011 | Suh .................... A61B 17/7065 |
| | | 623/17.12 |
| 2012/0316645 A1 | 12/2012 | Grotz |
| 2013/0018479 A1 | 1/2013 | Grotz |
| 2013/0116794 A1* | 5/2013 | Shohat ............... A61F 2/30756 |
| | | 623/19.11 |
| 2013/0211529 A1 | 8/2013 | Frauens et al. |
| 2014/0074245 A1* | 3/2014 | Shohat ............... A61F 2/30756 |
| | | 623/19.13 |
| 2014/0114426 A1 | 4/2014 | Forsell |
| 2014/0128974 A1 | 5/2014 | Bromer |
| 2014/0343675 A1* | 11/2014 | Vanleeuwen ....... A61F 2/30756 |
| | | 623/14.12 |
| 2016/0256286 A1* | 9/2016 | Morris .................. A61B 17/56 |
| 2016/0262901 A1* | 9/2016 | Vanleeuwen ....... A61F 2/30756 |
| 2018/0028326 A1* | 2/2018 | Vanleeuwen ....... A61F 2/30756 |

FOREIGN PATENT DOCUMENTS

| | | |
|---|---|---|
| WO | 2010127854 A1 | 11/2010 |
| WO | 2012017438 A1 | 2/2012 |

\* cited by examiner

BALLOON IMPLANT DEVICE

PRIORITY

The present application claims the benefit under 35 U.S.C. 120 of U.S. patent application Ser. No. 15/162,148 (filed May 23, 2016), which claims the benefit under 35 U.S.C. § 120 of U.S. patent application Ser. No. 14/213,009 (filed Mar. 14, 2014), which claims the benefit of U.S. Provisional App. No. 61/786,263 (filed Mar. 14, 2013), which are incorporated herein by reference.

FIELD OF THE INVENTION

The present invention is directed generally toward implant devices, and more particularly to a balloon implant device configured for placement in the shoulder area of an individual.

BACKGROUND OF THE INVENTION

Medical practitioners often see patients with ailments caused by soft or hard tissue displacements relative to the surrounding anatomy. Much effort is placed into repositioning the tissue and keeping it in the correct location. A common example is a broken bone, where the doctor repositions the bone and restricts its movement via a cast until the bones are healed.

Shoulder impingement is a clinical syndrome which occurs when the tendons of the rotator cuff muscles become irritated and inflamed as they pass through the passage between the acromion and the humerus, also called the subacromial space. Anything which causes narrowing of this space can result in pain and decreased range of motion.

Impingement can be caused by bony structures such as subacromial spurs (bony projections from the acromion), osteoarthritic spurs on the acromioclavicular joint, variations in the shape of the acromion, thickening or calcification of the coracoacromial ligament or thickening of the subacromial bursa. Likewise, injury or loss of strength of the rotator cuff muscles may cause the humerus to move superiorly, resulting in impingement.

Impingement is usually treated conservatively. Conservative treatment includes rest, cessation of painful activity, and physiotherapy. Physiotherapy treatments would typically focus at maintaining range of movement, improving posture, strength of the muscles of the shoulder and scapula, and reduction of pain. Physiotherapists may employ joint mobilization, interferential therapy, acupuncture, soft tissue therapy, therapeutic taping and scapular and rotator cuff strengthening to improve pain and function. Non-steroidal anti-inflammatory drugs (NSAIDs) and ice packs may also be used for pain relief. Therapeutic injections of corticosteroid and local anesthetic may be used to treat pain from persistent impingement. The total number of injections is generally limited to three due to possible side effects from the corticosteroid. Corticosteroids may cause musculoskeletal disorders. Because of these limitations, conservative treatments have a low success rate.

Surgical interventions may be available to remove the impinging structures, and the subacromial space may be widened by resection of the distal clavicle and excision of osteophytes on the under-surface of the acromioclavicular joint. Also damaged rotator cuff muscles can be surgically repaired. A variety of different devices are used to reposition tissue, such as casts and splints, screws and plates, and spacers such as those used in the spine. These devices may be inadequate for heavily articulatable joints such as the shoulder.

Consequently, it would be advantageous if an apparatus existed that is suitable for maintaining or widening a subacromial space to prevent or treat impingement in heavily articulated joints.

SUMMARY OF THE INVENTION

Accordingly, the present invention is directed to a novel method and apparatus for maintaining or widening a subacromial space to prevent or treat impingement in heavily articulated joints.

The present invention is directed to a balloon implant device. In one embodiment, a balloon implant device may be configured for placement in the shoulder area and may prevent impingement of a humeral head on a corresponding acromion. The balloon implant may be adjustable by adding or removing fluid from the balloon after implantation.

Another embodiment of the present invention is a kit including a balloon implant device, a placement measuring device and a plurality of spinal needles for identifying anatomical landmarks for the placement measuring device.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles.

BRIEF DESCRIPTION OF THE DRAWINGS

The numerous advantages of the present invention may be better understood by those skilled in the art by reference to the accompanying figures in which.

DETAILED DESCRIPTION OF THE INVENTION

Reference will now be made in detail to the subject matter disclosed, which is illustrated in the accompanying drawings. The scope of the invention is limited only by the claims; numerous alternatives, modifications and equivalents are encompassed. For the purpose of clarity, technical material that is known in the technical fields related to the embodiments has not been described in detail to avoid unnecessarily obscuring the description.

Figure 1:
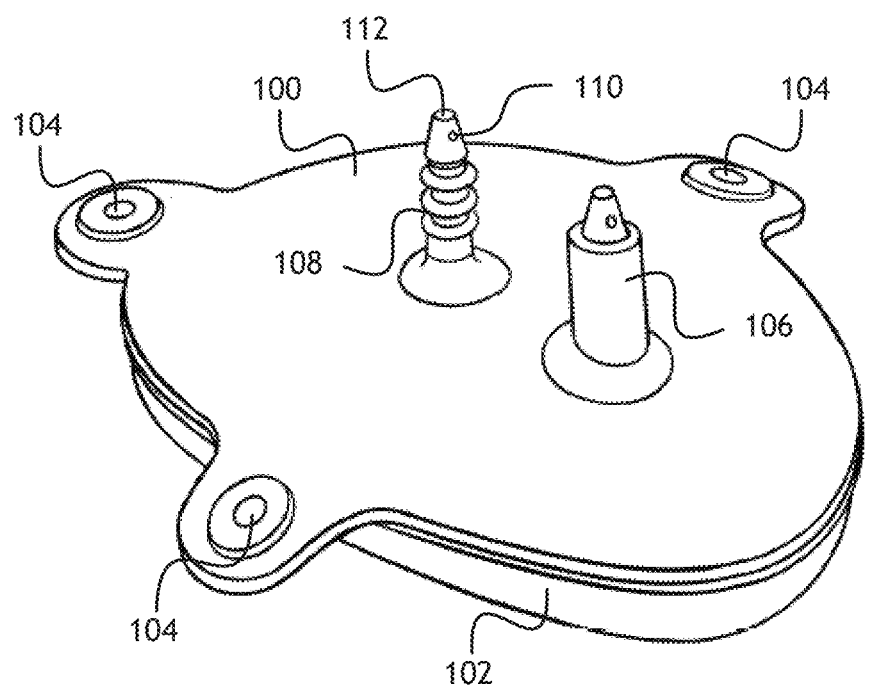
FIG. 1 shows a perspective view of an implant according to one embodiment of the present invention.

Referring to FIG. 1, a perspective view of an implant according to one embodiment of the present invention is shown. The implant is configured to be inserted between an acromion and humerus in a patient's shoulder. The implant maintains or expands the subacromial space to prevent impingement. The implant may also maintain the position of the humerus relative to the acromion to treat non-repairable rotator cuff injuries.

The implant may include an inflatable humeral balloon 102, the inflatable humeral balloon 102 configured to abut a humeral head and allow the humerus to move normally relative to the corresponding acromion and glenoid.

To anchor the implant, the implant may include one or more fixation features 104, 106, 108 disposed on the inflatable humeral balloon 102. The one or more fixation features 104, 106, 108 may include acromion anchors 106, 108. During implantation, anchor holes may be drilled in an acromion at appropriate locations, and the acromion anchors 106, 108 inserted through the anchor holes. In at least one embodiment, the acromion anchors 106, 108 may include suture holes 110 to receive sutures which may be threaded through the anchor holes in the acromion during implantation to help guide the acromion anchors 106, 108. The acromion anchors 106, 108 may include some mechanism, such as a friction inducing element, for retaining the acromion anchors 106, 108 in the anchor holes. Friction inducing elements may include vertical or radial ribs, a compression sleeve, or some similar mechanism. At least one acromion anchor 106, 108 may be configured as a valve to allow injection of a fluid into the inflatable humeral balloon 102. A valve according to at least one embodiment of the present invention allows multiple needle punctures to add or remove fluid during the operative lifetime of the implant. Furthermore, when implanted, the valve may be positioned in the acromion to be accessible by a needle without additional surgical intervention. Each acromion anchor 106, 108 may include an anchor hole insertion tip 112 configured to aid insertion of the acromion anchors 106, 108 into the anchor holes. After the implant is in position, the anchor hole insertion tips 112 may be cut-off such that they are substantially flush with a superior surface of the acromion; that is, a surface distal to a corresponding humeral head.

The one or more fixation features 104, 106, 108 may also include suture anchors 104. Suture anchors 104 may allow a surgeon to attach the implant to one or more surrounding anatomical structures, such as the Coracoacromial (CA) ligament, coracoid, glenoid or, in some embodiments, the humeral head, if the surgeon believes such attachment is necessary.

In one embodiment, the one or more fixation features 104, 106, 108 are directly disposed on the inflatable humeral balloon 102. In another embodiment, the one or more fixation features 104, 106, 108 are disposed on a separate acromion fixation element 100. The acromion fixation element 100 is configured to abut the surface of an acromion superior to a corresponding humeral head. Where the implant includes a separate inflatable humeral balloon 102 and acromion fixation element 100, the inflatable humeral balloon 102 and acromion fixation element 100 may be welded or otherwise bonded into a single implantable element. In at least one embodiment, the inflatable humeral balloon 102 comprises a closed inflatable structure bonded to the acromion fixation element 100 around the perimeter of the inflatable humeral balloon 102. In another embodiment, the inflatable humeral balloon 102 may comprise an open expandable structure where the acromion fixation element 100 is bonded to the inflatable humeral balloon 102 such that the bonded structure forms a closed, inflatable implant. The inflatable humeral balloon 102 may be bonded to the acromion fixation element 100 through any means known in the art; for example, through RF welding or gluing.

A surface configured to abut an acromion may be configured or treated to facilitate bonding to the acromion through tissue ongrowth or ingrowth; for example through chemical treatment or surface texturing.

Figure 2:
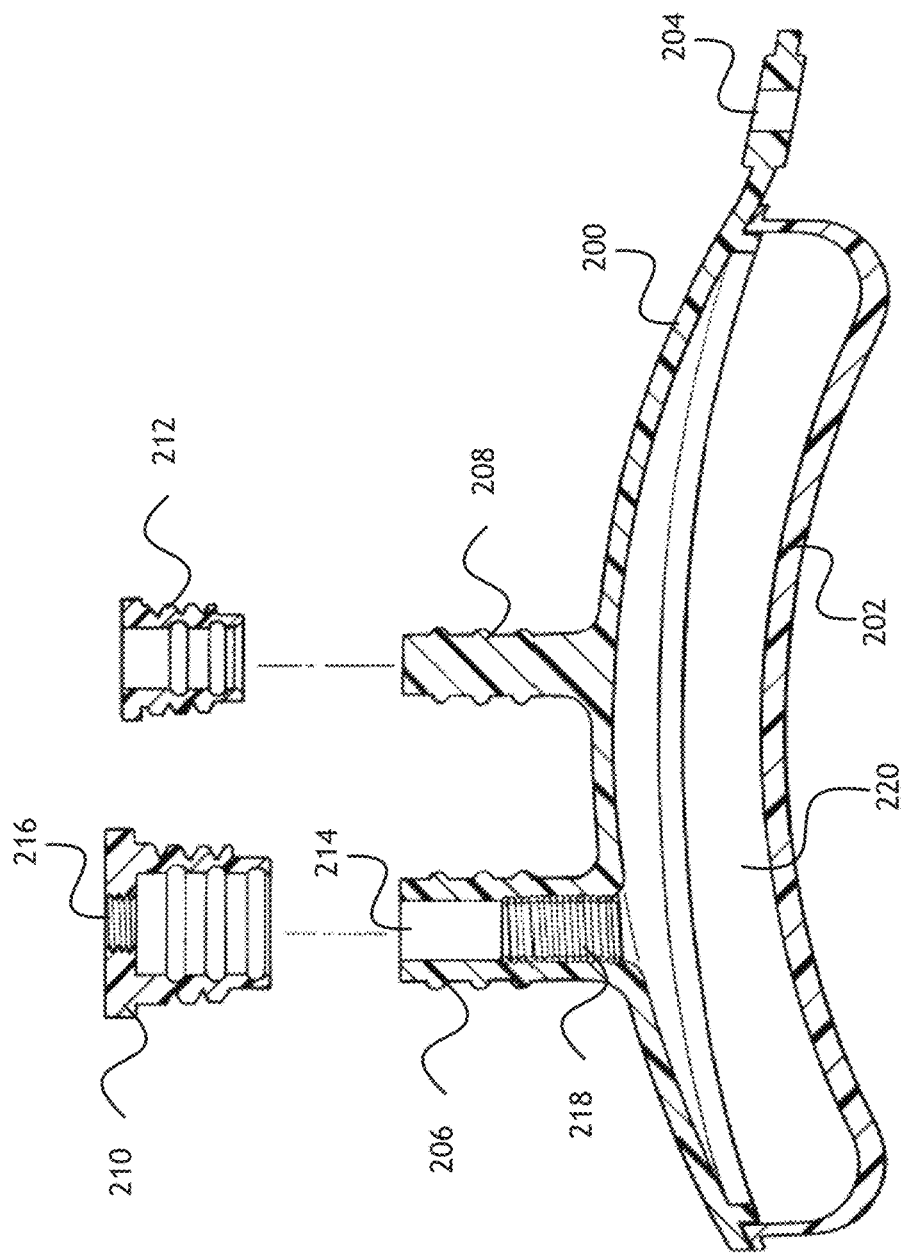
FIG. 2 shows a cross-sectional view of implant according to another embodiment of the present invention.

Referring to FIG. 2, a cross-sectional view of implant according to another embodiment of the present invention is shown. The implant may include an acromion fixation element 200 configured to abut the surface of an acromion superior to a corresponding humeral head. An inflatable humeral balloon 202 is welded or otherwise bonded to the acromion fixation element 200 such that, when implanted, the inflatable humeral balloon 202 is configured to abut a humeral head and allow the humerus to move normally relative to the corresponding acromion. The acromion fixation element 200 and the inflatable humeral balloon 202 define a fluid space 220 configured to hold a cushioning fluid. The implant may also include suture anchors 204 to allow a surgeon to attach the implant to one or more surrounding anatomical structures, such as the CA ligament, if the surgeon believes such attachment is necessary.

To anchor the implant to the acromion, the implant may include one or more acromion anchors 206, 208. In at least one embodiment, a first acromion anchor 206 may define a fill valve 214 to inject a fluid into the fluid space 220. At least a portion of the first acromion anchor 206 may comprise a compliant, implantable material such as silicone. In some embodiments of the present invention, the first acromion anchor 206 may be a structure configured to self-seal after being pierced by a needle. A compliant, implantable material may facilitate self-sealing in such embodiments. In one embodiment, the first acromion anchor 206 may include a valve support structure 218 to support the first acromion anchor 206 inside an anchor hole and hold the fill valve 214 open.

Each acromion anchor 206, 208 may be held in place in a corresponding anchor hole by a compression sleeve 210, 212. When an implant is placed in position, with acromion anchors 206, 208 inserted into anchor holes in an acromion, each compression sleeve 210, 212 may be inserted in to the anchor holes through a superior surface of the acromion such that the compression sleeves 210, 212 surround a corresponding acromion anchor 206, 208 and create a friction lock, interlocking geometry or some other locking mechanism between the acromion anchor 206, 208 and the acromion that defines the corresponding anchor hole. Alternatively, each compression sleeve 210, 212 may be inserted first with the corresponding acromion anchor 206, 208 being pulled through the compression sleeve 210, 212. Each compression sleeve 210, 212 may include a friction inducing element disposed on the periphery to further enhance the friction lock. In some embodiments, the friction inducing element may be a threaded portion configured to mechanically engage a threaded portion of the corresponding anchor hole or to produce a threaded portion in the corresponding anchor hole during insertion.

Where the implant includes a first acromion anchor 206 defining a fill valve 214, a corresponding first compression sleeve 210 may define a valve access port 216 accessible from the superior surface of the acromion when the implant is in position. The valve access port 216 may be a closable or sealable access element permitting access to the fill valve 214, and thereby allow fluid to be injected into the fluid space 220 after the implant is in position. Furthermore, the valve access port 216 defines a guide for maintaining a needle on a correct trajectory. Alternatively, the fill valve 214 may include a restrictive element similar to the valve access port 216 of the first compression sleeve 210, configured to maintain a needle on a correct trajectory. In another embodiment, a restrictive element similar to the valve access port 216 may be location in one of the acromion anchors 206.

When the implant is fully positioned and installed, the fill valve 214 may be located just beneath superficial soft tissue superior to acromion bone. Such positioning is convenient to allow adjustments to the fluid volume in the fluid space 220. After the initial surgery, adjustments may be made without a secondary surgery. If the surgeon feels that the balloon volume is too small (underfill) or too large (overfill), the surgeon may inject or remove fluid from the fluid space 220 with an appropriate tool (such as a needle) through the soft tissue superior to acromion bone. The subacromial space could also be made larger progressively over time through a series of volume adjustments if this space is severely contracted.

While the implant shown in FIG. 2 comprises an acromion fixation element 200 and an inflatable humeral balloon 202, a person skilled in the art may appreciate that the implant may comprise a single inflatable element defining the fluid space 220, with fixation features 204, 206, 208 disposed on the surface of the single inflatable element.

Figure 3:
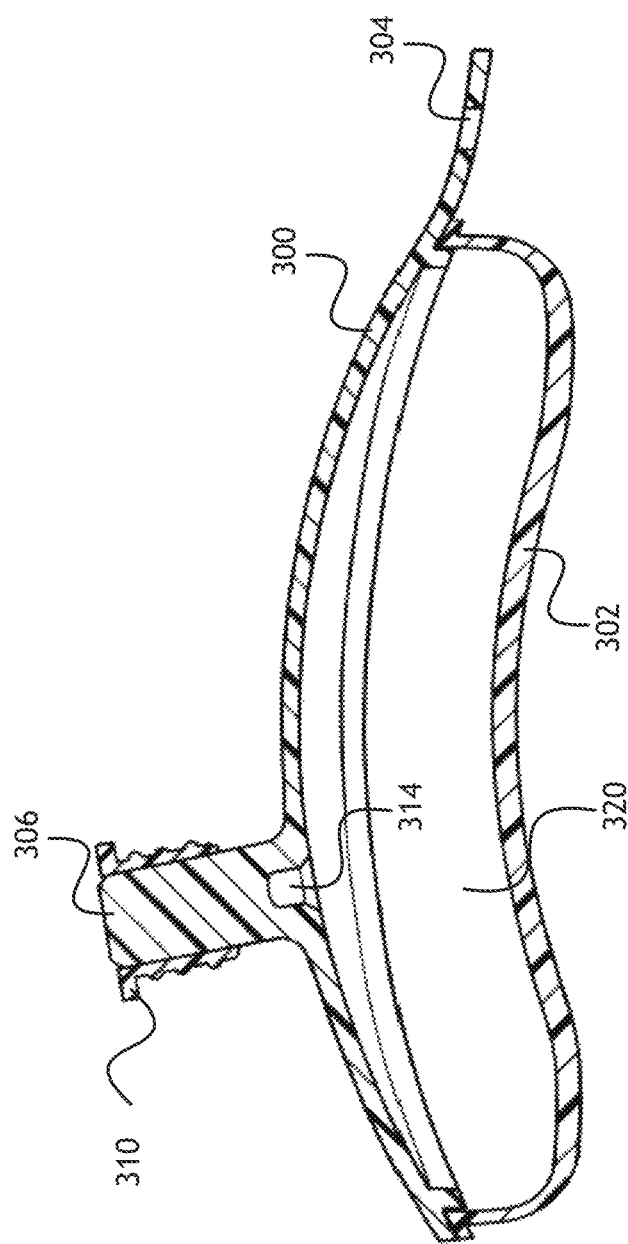
FIG. 3 shows a cross-sectional view of implant according to another embodiment of the present invention.

Referring to FIG. 3, a cross-sectional view of implant according to another embodiment of the present invention is shown. The implant may include an acromion fixation element 300 configured to abut the surface of an acromion superior to a corresponding humeral head. An inflatable humeral balloon 302 is welded or otherwise bonded to the acromion fixation element 300 such that, when implanted, the inflatable humeral balloon 302 is configured to abut a humeral head and allow the humerus to move normally relative to the corresponding acromion. The acromion fixation element 300 and the inflatable humeral balloon 302 define a fluid space 320 configured to hold a cushioning fluid. The implant may also include suture anchors 304 to allow a surgeon to attach the implant to one or more surrounding anatomical structures, such as the CA ligament, if the surgeon believes such attachment is necessary.

To anchor the implant to the acromion, the implant may include one or more acromion anchors 306. In at least one embodiment, the one or more acromion anchors 306 may define a fill valve 314 to inject or remove a fluid into or from the fluid space 320. In one embodiment, the acromion anchor 306 is pierced by a needle to access the fill valve 314 and inject or remove the fluid.

The one or more acromion anchors 306 may be held in place in a corresponding anchor hole by a compression sleeve 310. When an implant is placed in position, with acromion anchors 306 inserted into anchor holes in an acromion, each compression sleeve 310 may be inserted in to the anchor holes through a superior surface of the acromion such that the compression sleeve 310 surrounds a corresponding acromion anchor 306 and create a friction lock, threaded engaging portion, snapping portion, locking geometry or other appropriate mechanism between the acromion anchor 306 and the acromion that defines the corresponding anchor hole. Furthermore, the compression sleeve 310 may create or enhance a compression force on a corresponding acromion anchor 306 to close a needle puncture to a fill valve 314 after fluid is injected into the fluid space 320.

While the implant shown in FIG. 3 comprises an acromion fixation element 300 and an inflatable humeral balloon 302, a person skilled in the art may appreciate that the implant may comprise a single inflatable element defining the fluid space 3220, with fixation features 304, 306 disposed on the surface of the single inflatable element.

Figure 4:
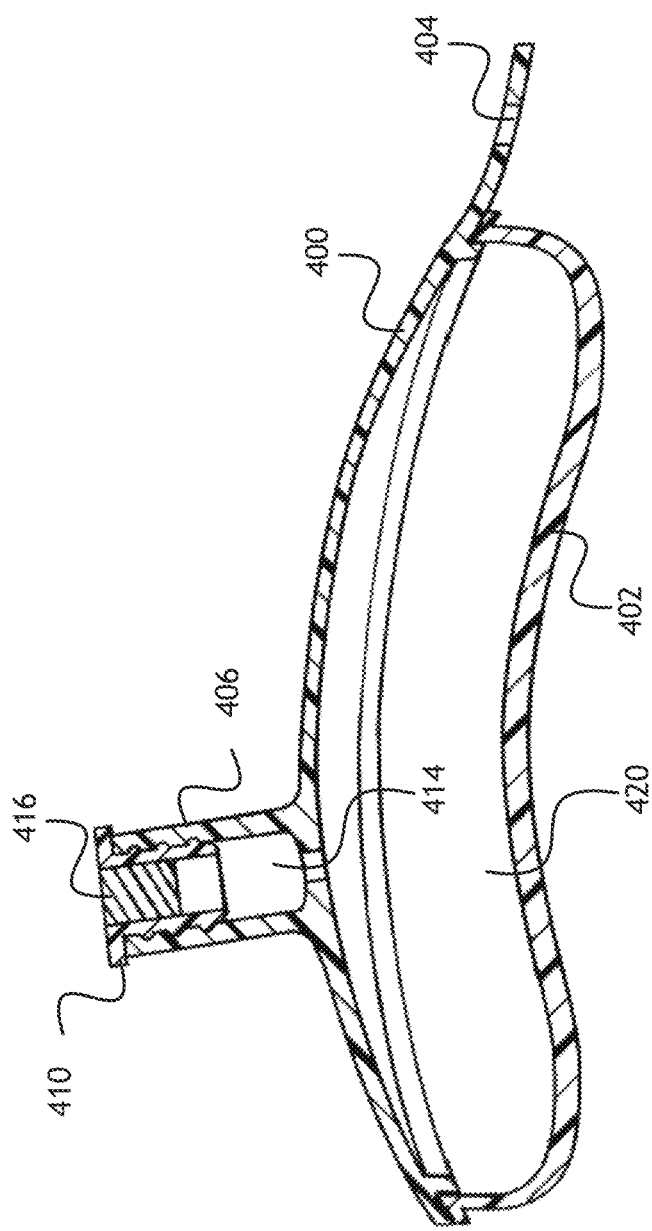
FIG. 4 shows a cross-sectional view of implant according to another embodiment of the present invention.

Referring to FIG. 4, a cross-sectional view of implant according to another embodiment of the present invention is shown. The implant may include an acromion fixation element 400 configured to abut the surface of an acromion superior to a corresponding humeral head. An inflatable humeral balloon 402 is welded or otherwise bonded to the acromion fixation element 400 such that, when implanted, the inflatable humeral balloon 402 is configured to abut a humeral head and allow the humerus to move normally relative to the corresponding acromion. The acromion fixation element 400 and the inflatable humeral balloon 402 define a fluid space 420 configured to hold a cushioning fluid. The implant may also include suture anchors 404 to allow a surgeon to attach the implant to one or more surrounding anatomical structures, such as the CA ligament, if the surgeon believes such attachment is necessary.

To anchor the implant to the acromion, the implant may include one or more acromion anchors 406. In at least one embodiment, the one or more acromion anchors 406 may define a fill valve 414 to inject a fluid into the fluid space 420. The one or more acromion anchors 406 may be held in place in a corresponding anchor hole by an expansion insert 410. When an implant is placed in position, with acromion anchors 406 inserted into anchor holes in an acromion, each expansion insert 410 may be inserted into the fill valve 414 defined by the acromion anchors 406 to create or enhance a friction lock between the acromion anchors 406 and the acromion that defines the corresponding anchor hole. An expansion insert 410 may define a valve access port 416 accessible from the superior surface of the acromion when the implant is in position. The valve access port 416 may be a closable or sealable access element permitting access to the fill valve 414, and thereby allow fluid to be injected into the fluid space 420 after the implant is in position.

While the implant shown in FIG. 4 comprises an acromion fixation element 400 and an inflatable humeral balloon 402, a person skilled in the art may appreciate that the implant may comprise a single inflatable element defining the fluid space 420, with fixation features 404, 406 disposed on the surface of the single inflatable element.

Figure 5:
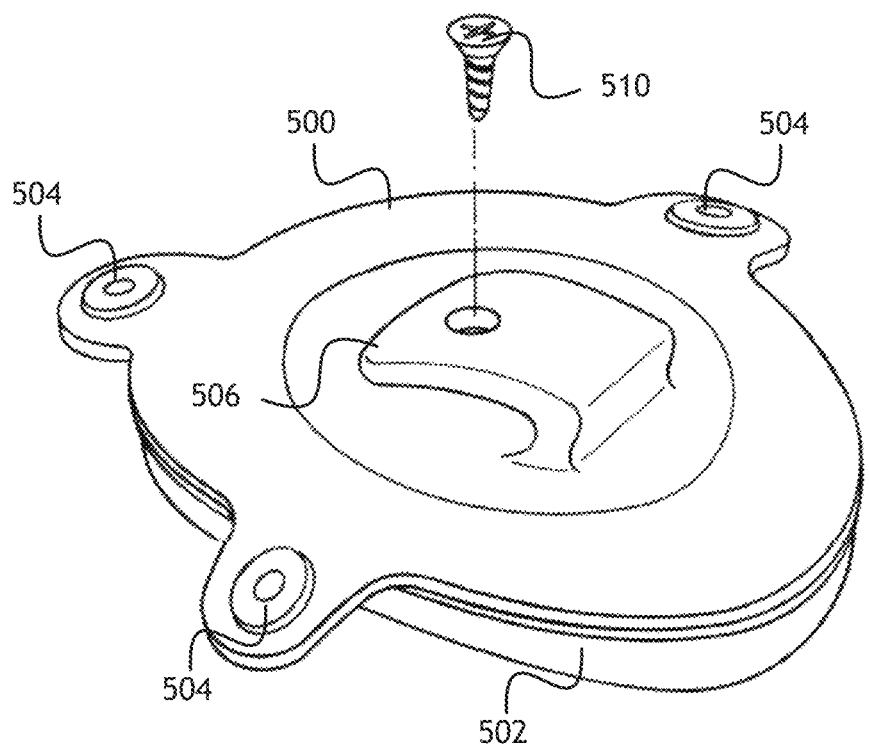
FIG. 5 shows a perspective view of another implant according to one embodiment of the present invention.

Referring to FIG. 5, a perspective view of another implant according to one embodiment of the present invention is shown. The implant may include an acromion fixation element 500 configured to abut the surface of an acromion superior to a corresponding humeral head. The surface of the acromion fixation element 500 may be configured to facilitate bonding to the acromion through tissue ongrowth or ingrowth; for example, through chemical treatment or surface texturing. An inflatable humeral balloon 502 is welded or otherwise bonded to the acromion fixation element 500 such that, when implanted, the inflatable humeral balloon 502 is configured to abut a humeral head and allow the humerus to move normally relative to the corresponding acromion. In at least one embodiment, the inflatable humeral balloon 502 is bonded to the acromion fixation element 500 around the perimeter of the inflatable humeral balloon 502. The implant may also include suture anchors 504. Suture anchors 504 may allow a surgeon to attach the implant to one or more surrounding anatomical structures, such as the CA ligament, if the surgeon believes such attachment is necessary.

To anchor the implant to the acromion, the implant may include one or more acromion brackets 506. The one or more acromion brackets 506 wrap around one edge of the acromion to lay against the superior surface of the acromion while the acromion fixation element 500 abuts the inferior surface of the acromion. The one or more acromion brackets 506 may be secured to the acromion with corresponding bracket screws 510.

While the implant shown in FIG. 5 comprises an acromion fixation element 500 and an inflatable humeral balloon 502, a person skilled in the art may appreciate that the implant may comprise a single inflatable element defining a fluid space, with fixation features 504, 506 disposed on the surface of the single inflatable element.

Figure 6:
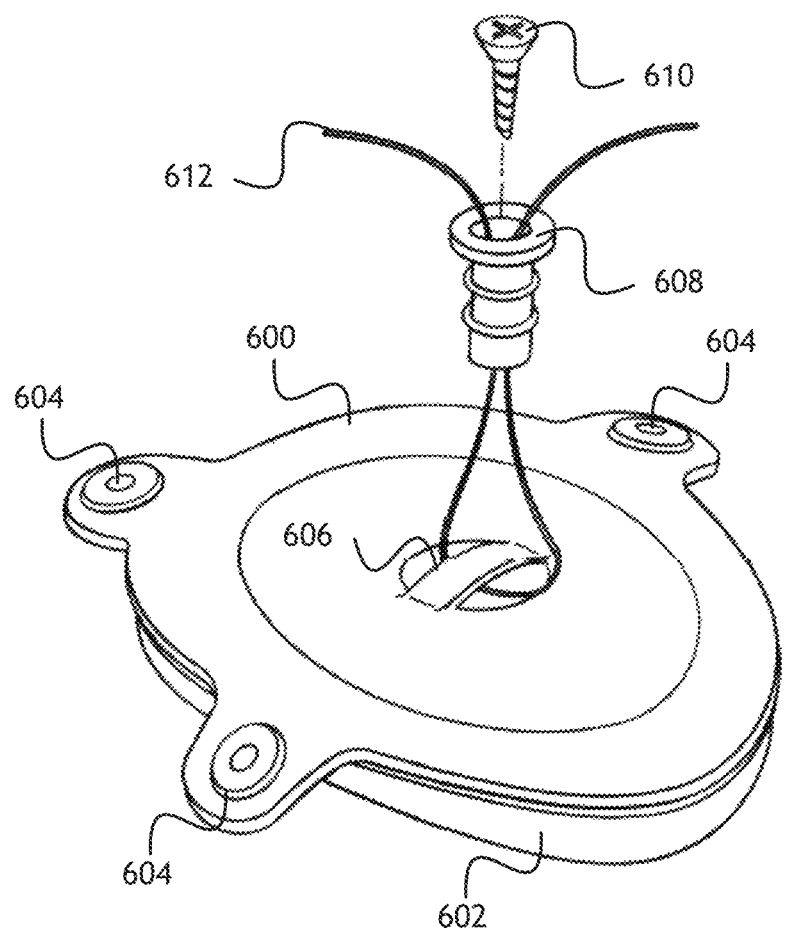
FIG. 6 shows a perspective view of another implant according to one embodiment of the present invention.

Referring to FIG. 6, a perspective view of another implant according to one embodiment of the present invention is shown. The implant may include an acromion fixation element 600 configured to abut the surface of an acromion superior to a corresponding humeral head. The surface of the acromion fixation element 600 may be configured to facilitate bonding to the acromion through tissue ongrowth or ingrowth; for example, through chemical treatment or surface texturing. An inflatable humeral balloon 602 is welded or otherwise bonded to the acromion fixation element 600 such that, when implanted, the inflatable humeral balloon 602 is configured to abut a humeral head and allow the humerus to move normally relative to the corresponding acromion. In at least one embodiment, the inflatable humeral balloon 602 is bonded to the acromion fixation element 600 around the perimeter of the inflatable humeral balloon 602. The implant may also include suture anchors 604. Suture anchors 604 may allow a surgeon to attach the implant to one or more surrounding anatomical structures, such as the CA ligament, if the surgeon believes such attachment is necessary.

To anchor the implant to the acromion, the implant may include one or more suture brackets 606. The one or more suture brackets 606 are configured to receive a corresponding suture loop 612. During implantation, suture holes may be drilled at predetermined locations in an acromion, and suture lock rings 608 inserted in each suture hole. A suture loop 612 may be passed through each suture bracket 606 and the through a suture hole and corresponding suture lock ring 608 from the inferior side of the acromion to the superior side of the acromion. When the implant is properly positioned between the acromion and the humeral head of a corresponding humerus, each suture loop 612 may be locked in place relative to a corresponding suture lock ring 608 with a suture lock screw 610.

While the implant shown in FIG. 6 comprises an acromion fixation element 600 and an inflatable humeral balloon 602, a person skilled in the art may appreciate that the implant may comprise a single inflatable element defining a fluid space, with fixation features 604, 606 disposed on the surface of the single inflatable element.

Figure 7:
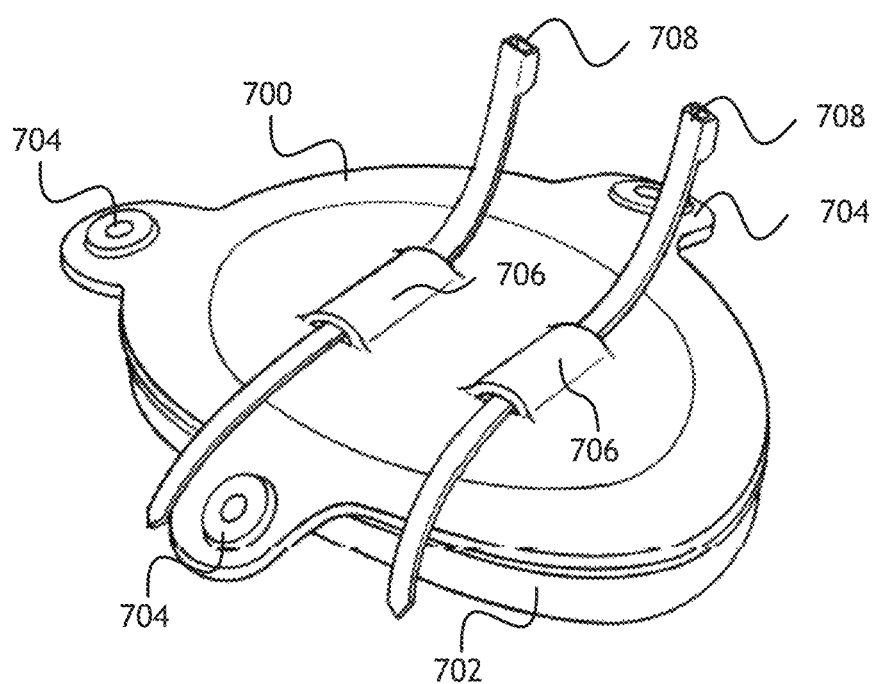
FIG. 7 shows a perspective view of another implant according to one embodiment of the present invention.

Referring to FIG. 7, a perspective view of another implant according to one embodiment of the present invention is shown. The implant may include an acromion fixation element 700 configured to abut the surface of an acromion superior to a corresponding humeral head. The surface of the acromion fixation element 700 may be configured to facilitate bonding to the acromion through tissue ongrowth or ingrowth; for example, through chemical treatment or surface texturing. An inflatable humeral balloon 702 is welded or otherwise bonded to the acromion fixation element 700 such that, when implanted, the inflatable humeral balloon 702 is configured to abut a humeral head and allow the humerus to move normally relative to the corresponding acromion. In at least one embodiment, the inflatable humeral balloon 702 is bonded to the acromion fixation element 700 around the perimeter of the inflatable humeral balloon 702. The implant may also include suture anchors 704. Suture anchors 704 may allow a surgeon to attach the implant to one or more surrounding anatomical structures, such as the CA ligament, if the surgeon believes such attachment is necessary.

To anchor the implant to the acromion, the implant may include one or more strap brackets 706. The one or more strap brackets 706 may be substantially the same width as a patient's acromion. Each of the one or more strap brackets 706 are configured to receive a corresponding acromion strap 708. When the implant is properly positioned, the acromion straps 708 wrap around the acromion and are self-secured to hold the implant in place. In at least one embodiment, the acromion straps 708 may be surgically implantable zip ties.

While the implant shown in FIG. 7 comprises an acromion fixation element 700 and an inflatable humeral balloon 702, a person skilled in the art may appreciate that the implant may comprise a single inflatable element defining a fluid space, with fixation features 704, 706 disposed on the surface of the single inflatable element.

Figure 8:
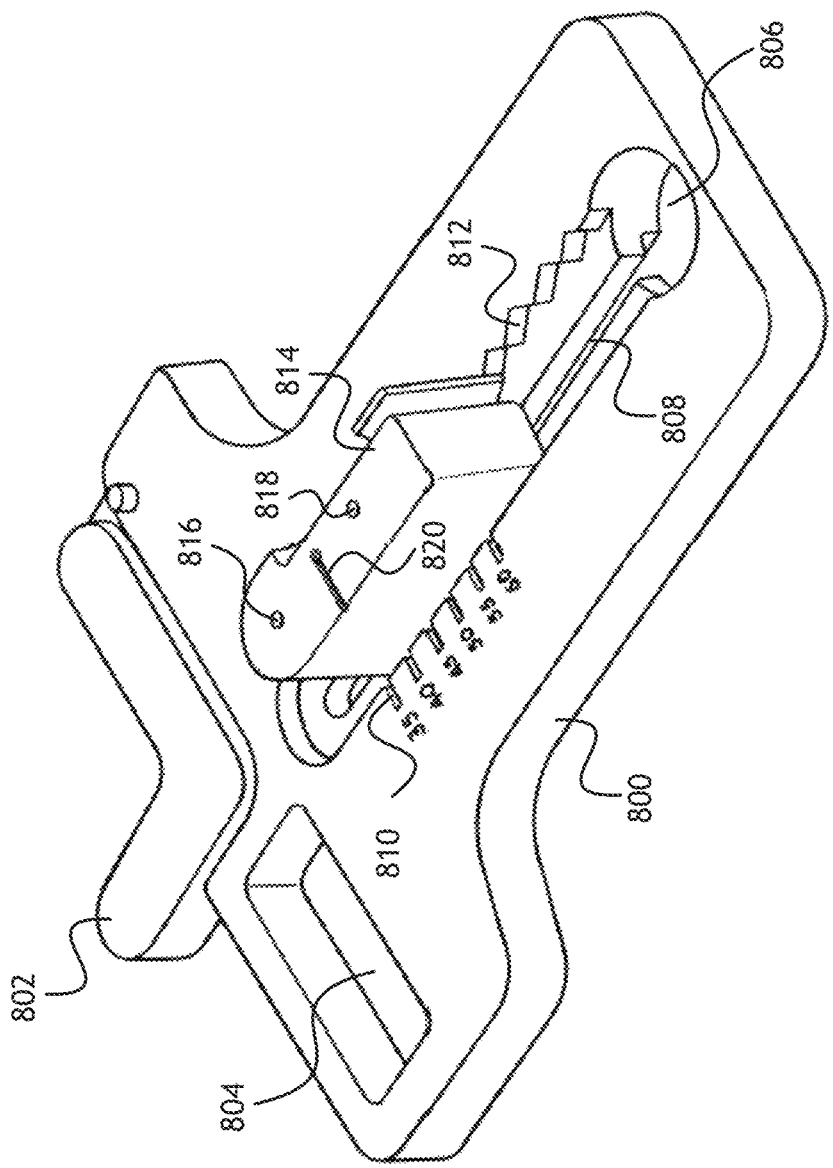
FIG. 8 shows a perspective view of an implant locating device for placing an implant according to at least one embodiment of the present invention.
Figure 9:
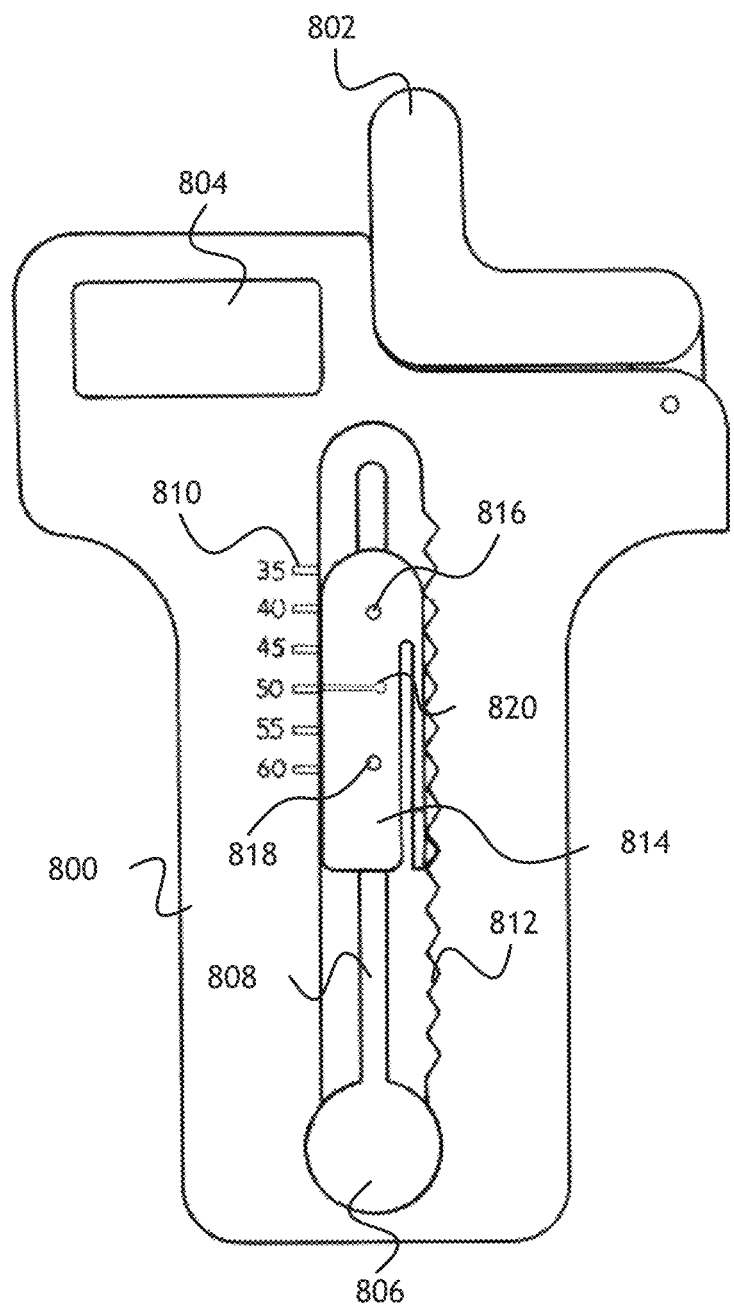
FIG. 9 shows a top view of the implant locating device for placing an implant according to at least one embodiment of the present invention shown in FIG. 8.

Referring to FIG. 8 and FIG. 9, a perspective view and a top view of an implant locating device 800 for placing an implant according to at least one embodiment of the present invention are shown. The implant locating device 800 may be configured to align one or more drill sites in a patient's acromion to certain anatomical features in the patient during surgery. Such drill holes may comprise anchor holes or suture holes as further described herein.

The implant locating device 800 may include a plurality of placement pin guides 804, 806 and placement pin locking lever 802. During implantation, placement pins are positioned to mark certain anatomical features of an acromion. In at least one embodiment, two placement pins (spinal needles) may be placed at the anterior edge of the acromion and one placement pin may be placed at the posterior edge of the acromion. The distance from the anterior placement pins to the posterior placement pin defines the anterior-to-posterior length (LAP) measurement.

Once the placement pins are in position, the implant locating device 800 may be positioned such that a first placement pin guide 806 may receive the posterior placement pin. The posterior placement pin may then move along a pin/slider channel 808 as necessary to allow a second placement pin guide 804 to be placed over a first anterior placement pin. The placement pin locking lever 802 may be opened so that a second anterior placement pin may be positioned between the placement pin locking lever 802 and the body of the implant locating device 800. The implant locating device 800 is then placed against the superior surface of the acromion and the placement pin locking lever 802 is closed to hold the implant locating device in position relative to the placement pins.

Once the implant locating device 800 is locked in position, a drill hole slider 814 defining one or more marker holes 816, 818 may be moved along the pin/slider channel 808. The drill hole slider 814 may include a mechanism to engage a slider locking element 812 along the pin/slider channel 808, such as saw tooth structure, to hold the drill hole slider 814 in place while marking drill holes. The drill hole slider 814 may be positioned based on the LAP measurement. LAP measurement indicators 810 on the implant locating device 800 may indicate the proper position of the drill hole slider 814 for various LAP measurements. A position indicator 820 on the drill hole slider 814 may be aligned with one of the LAP measurement indicators 810 based on the LAP measurement to position the one or more marker holes 816, 818 at desirable drill hole locations relative to the acromion.

The one or more marker holes 816, 818 are spaced relative to each other to correspond to features of an implant such as acromion anchors. Wires, such as Kirschner (K) wires, may be placed in the marker holes 816, 818 and into the underlying acromion to mark appropriate drilling positions. The implant locating device 800 may then be removed and an appropriately sized drill used to drill the holes. In some embodiments, a cannulated drill may be used.

Figure 10:
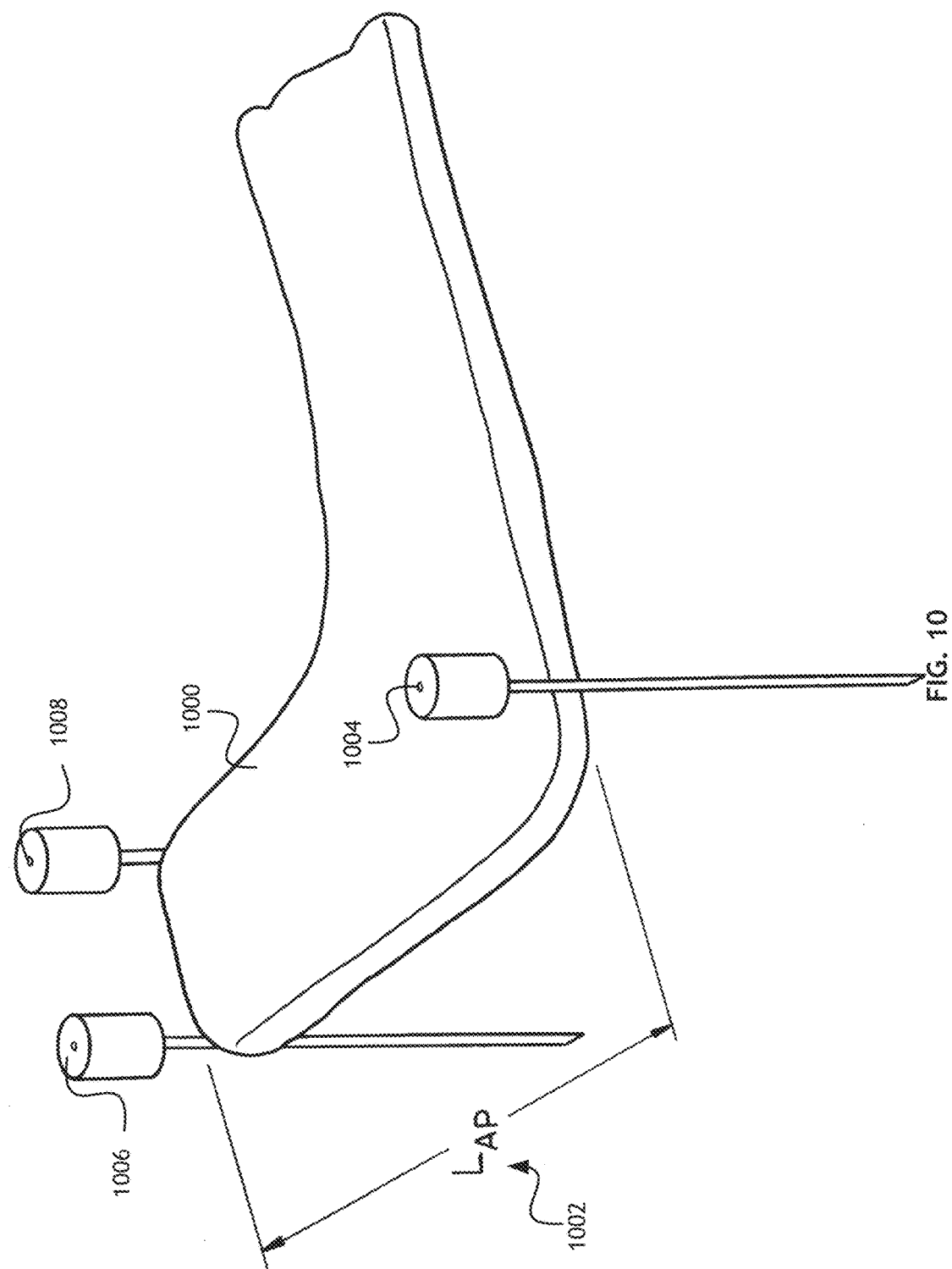
FIG. 10 shows a perspective, environmental view of a plurality of placement pins and a patient's acromion.

Referring to FIG. 10, a perspective, environmental view of a plurality of placement pins and a patient's acromion is shown. An implant according to the present invention must be positioned properly to be effective in reducing impingement. Proper placement depends on the relative anatomy of each patient; particularly the patient's acromion 1000. A plurality of placement pins 1004, 1006, 1008 are placed in tissue to mark certain anatomical landmarks of the patient's acromion 1000. In one embodiment, a posterior placement pin 1004 may mark a posterior edge of the acromion 1000, a first anterior placement pin 1006 may mark a distal, anterior edge of the acromion 1000 and a second anterior placement pin 1008 may mark a proximal, anterior edge of the acromion 1000. The first anterior placement pin 1006 and second anterior placement pin 1008 define an anterior line segment. The posterior placement pin 1004 may define a line orthogonal to the anterior line segment, bisecting the segment and thereby defining a centerline of a relevant portion of the acromion 1000. The distance from the anterior placement pins 1006, 1008 to the posterior placement pin 1004 defines an anterior-to-posterior length measurement (LAP) 1002. In another embodiment, a first acromioclavicular joint placement pin placed in proximity to a posterior portion of the acromioclavicular joint and a second acromioclavicular joint placement pin placed in a corresponding location on the lateral edge of the acromion may define a lateral line across the relevant portion of the acromion. The centerline defines a location on the acromion where at least one anchor hole is drilled.

In another embodiment, a first lateral acromial placement pin placed at a lateral anterior corner of the acromion and a first acromioclavicular joint placement pin placed in proximity to a posterior portion of the acromioclavicular joint define a first reference line. The intersection of the first reference line and an acromion midline defines the center location of the implant. A K-wire may be inserted at such location to facilitate the placement of a locating device to drill anchor holes as more fully defined herein.

Figure 11:
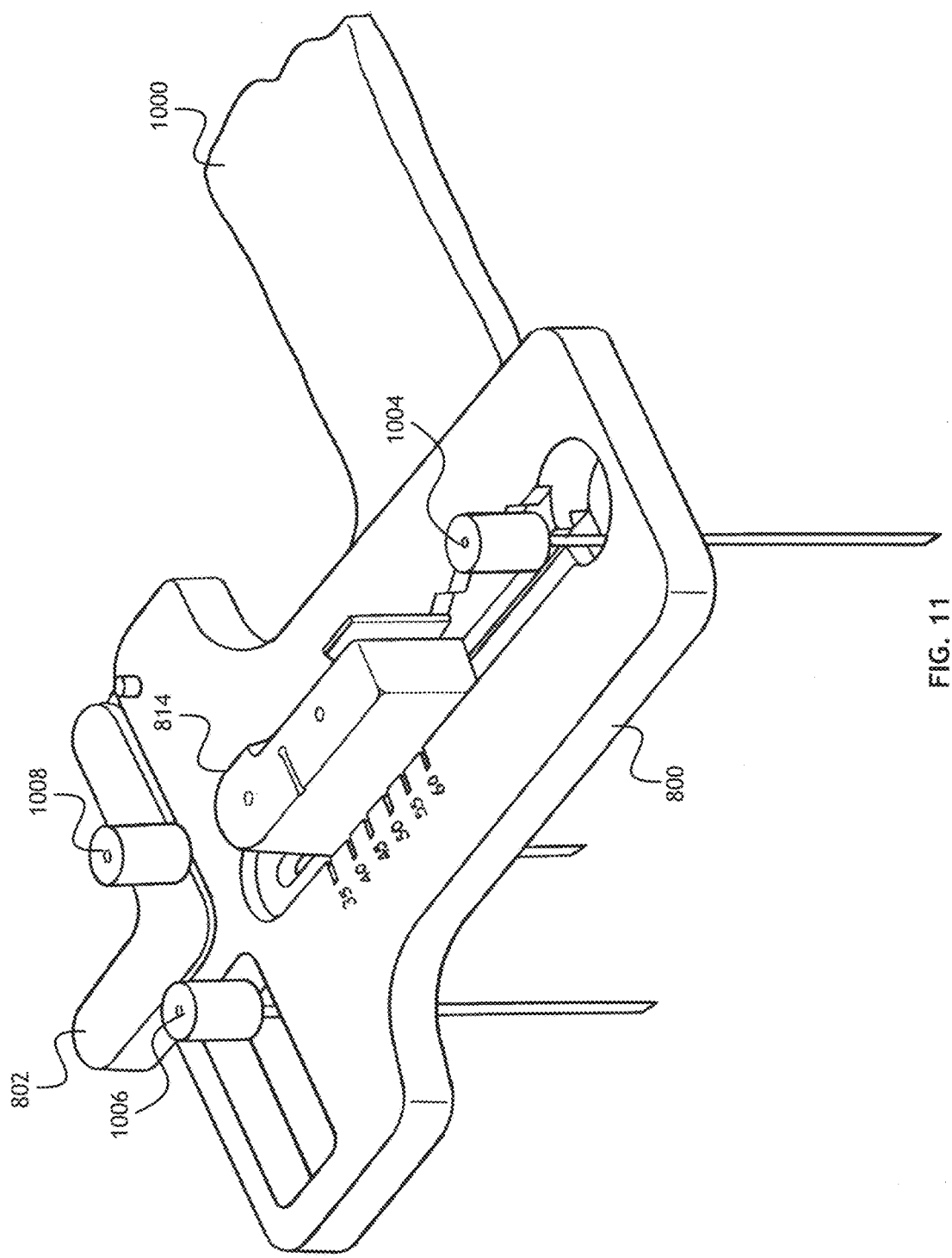
FIG. 11 shows a perspective, environmental view of the placement pins and acromion of FIG. 10, with an implant locating device such as in FIG. 8.

Referring to FIG. 11, a perspective, environmental view of the placement pins and acromion of FIG. 10, with an implant locating device such as in FIG. 8 is shown. When placement pins 1004, 1006, 1008 are in position relative to a patient's acromion 1000, an implant locating device 800 may be positioned using the placement pins 1004, 1006, 1008 as reference points. In at least one embodiment, a placement pin locking lever 802 may secure the implant locating device 800. A drill hole slide 814 in the implant locating device 800 may then be positioned in a pin/slider channel according to a LAP measurement derived from the placement pins 1004, 1006, 1008.

Figure 12:
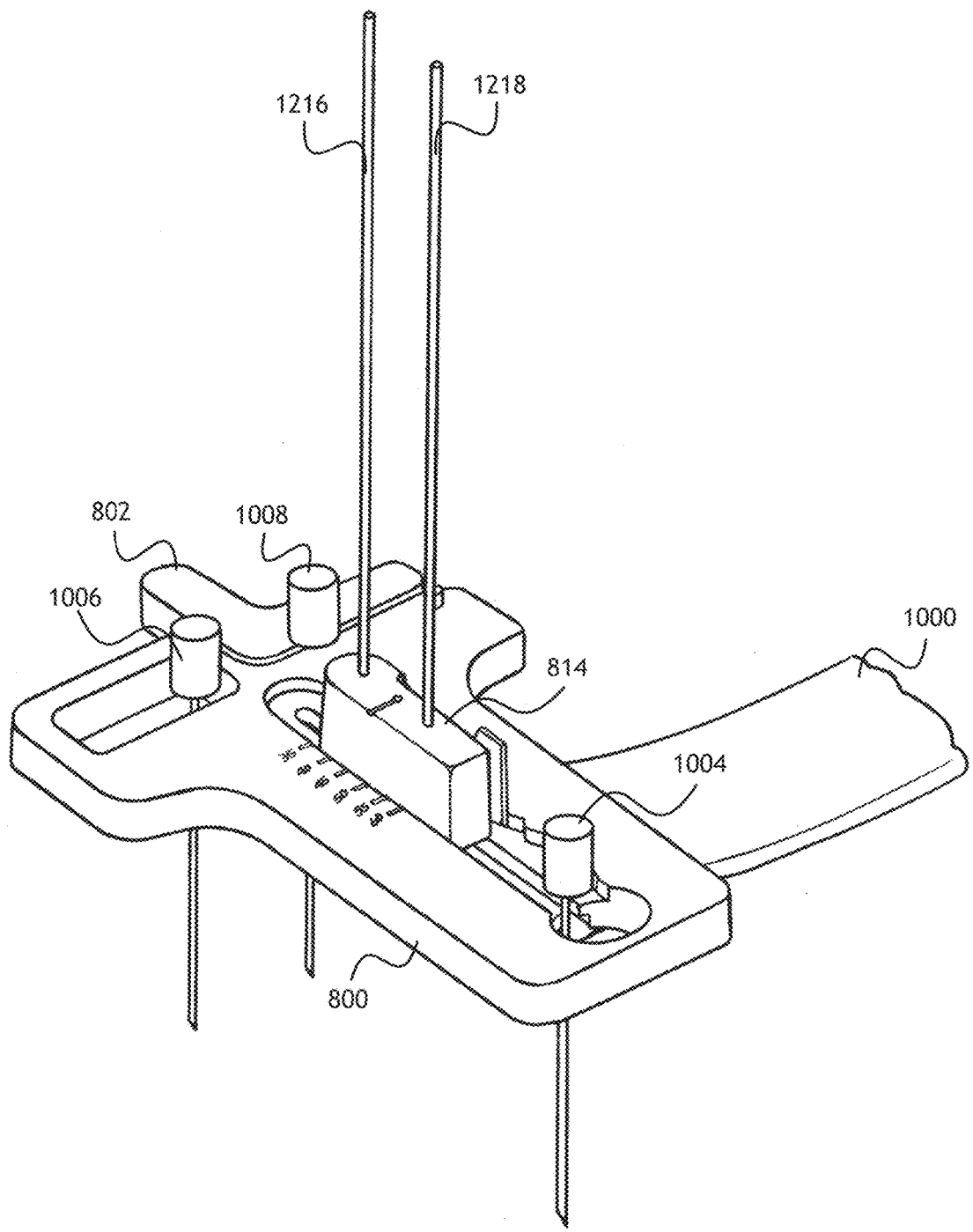
FIG. 12 shows a perspective, environmental view of the placement pins, acromion and implant locating device of FIG. 11 with K wires.

Referring to FIG. 12, a perspective, environmental view of the placement pins, acromion and implant locating device of FIG. 11 with K wires is shown. When an implant locating device 800 has been positioned relative to an acromion 1000 based on the locations of a plurality of placement pins 1004, 1006, 1008, and a drill hole slider 814 set according to a LAP measurement, anchor holes or suture holes may be marked and drilled in the acromion 1000. In at least one embodiment, K wires 1216, 1218 are inserted through holes in the drill hole slider 814 specifically configured to receive such K wires 1216, 1218. The K wires 1216, 1218 mark specific locations on the patient's acromion 1000 where holes may be drilled to allow or facilitate placement of an implant according to the present invention. Once the K wires 1216, 1218 are in position, the placement pin locking lever 802 may be released, and the implant locating device 800 removed, leaving the K wires 1216, 1218 in place. The placement pins 1004, 1006, 1008 may also be removed. A surgeon may then drill appropriately sized holes in the acromion 1000 at each site marked by the K wires 1216, 1218.

Figure 13:
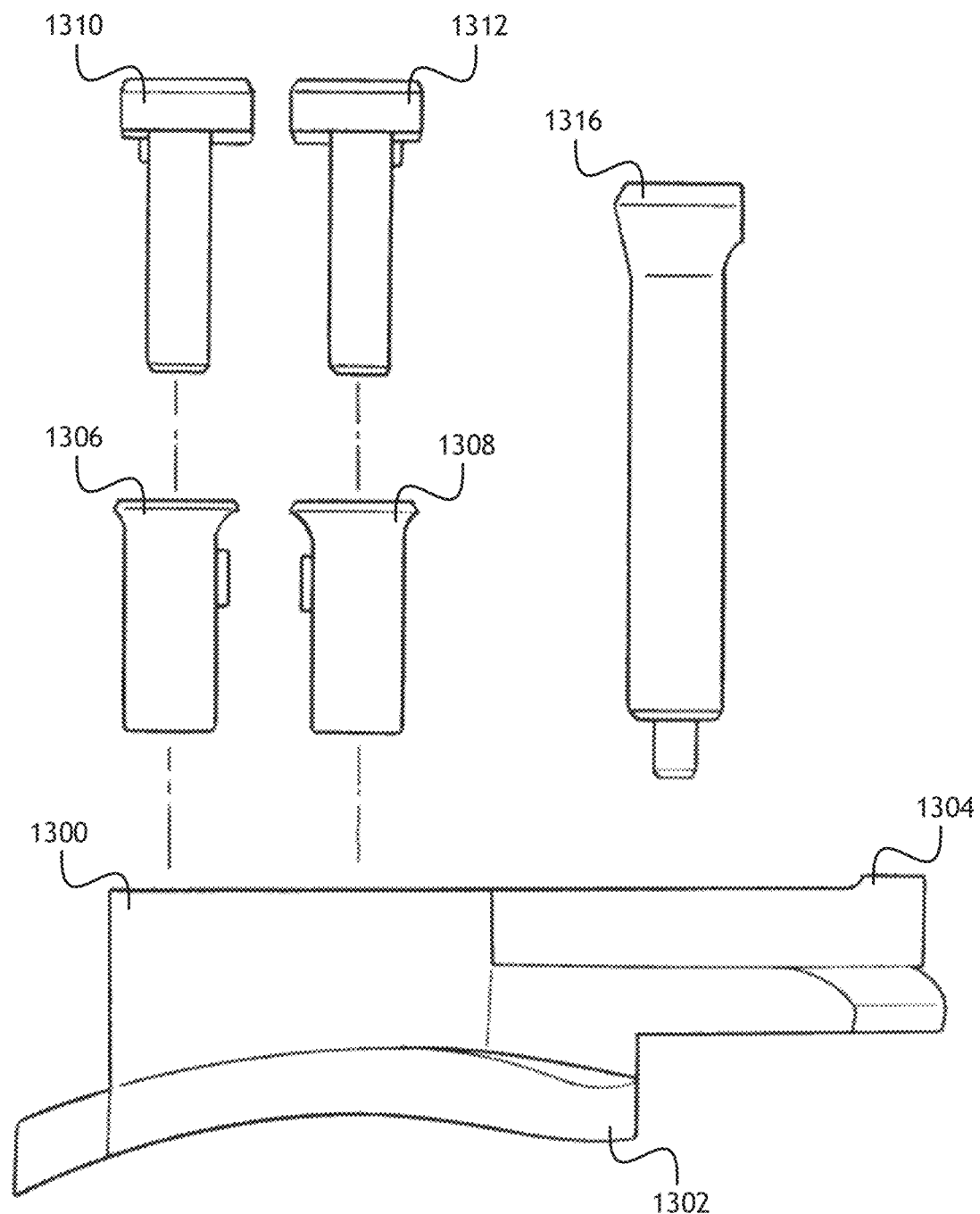
FIG. 13 shows a side view of an implant locating device kit for placing an implant according to at least one embodiment of the present invention.

Referring to FIG. 13, a side view of an implant locating device kit for placing an implant according to at least one embodiment of the present invention is shown. The locating device kit may include an implant locating device 1300 with an acromion conforming portion 1302 and a midline extension 1304. The implant locating device kit may include one or more drill guide inserts 1306, 1308 configured to fit into guide holes in the implant locating device 1300; furthermore, the implant locating device kit may include one or more wire guide plugs 1310, 1312 configured to fit into guide holes in the implant locating device 1300 or into the drill guide inserts 1306, 1308 to guide K-wires into appropriate locations along an acromial midline to identify drill hole locations in an acromion. The implant locating device kit may also include a drill plug 1316.

Figure 14:
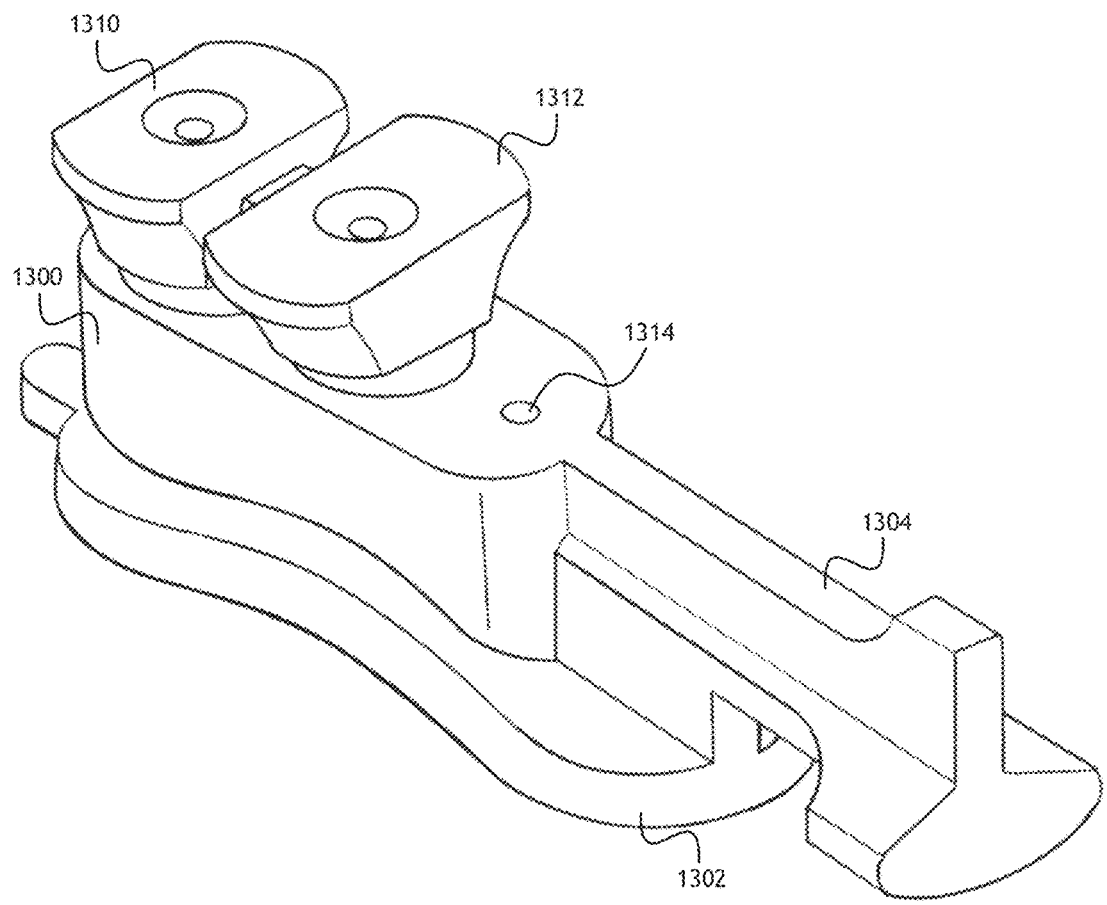
FIG. 14 shows a perspective view of the implant locating device in FIG. 13.
Figure 15:
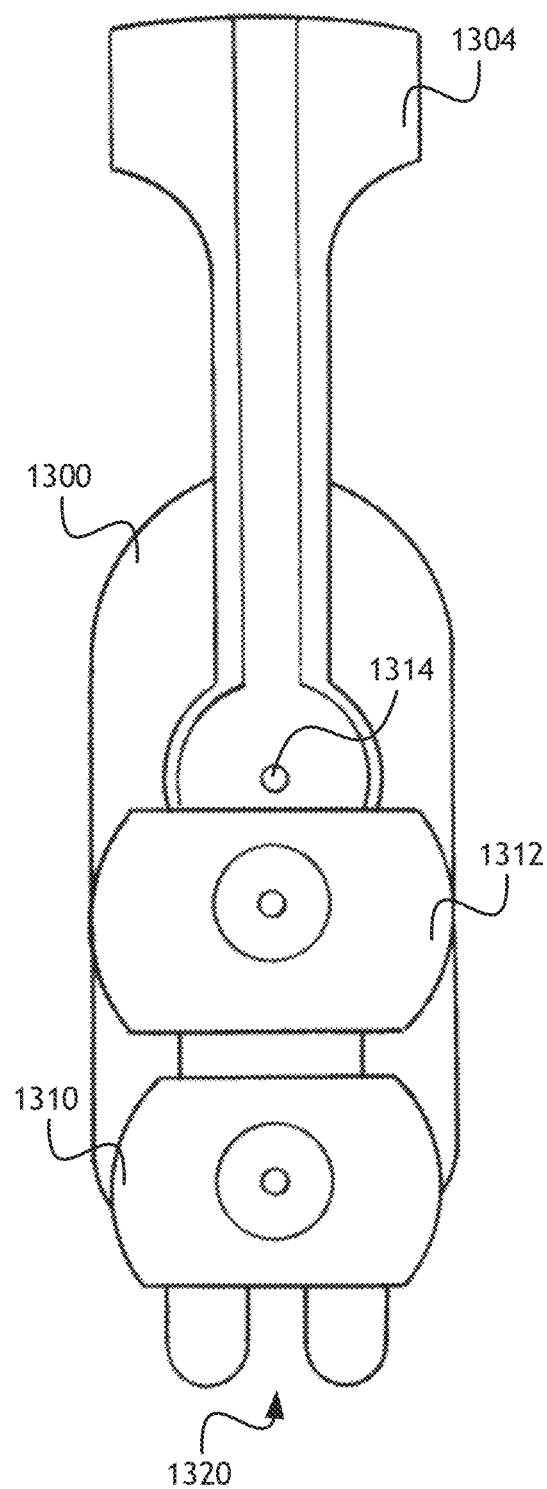
FIG. 15 shows a top view of the implant locating device in FIG. 13.

Referring to FIGS. 14 and 15, a perspective and a top view of the implant locating device in FIG. 13 are shown. In one embodiment, the implant placing device 1300 defines one or more guide holes (in a preferred embodiment, two guide holes) and a K-wire center placement hole 1314. In at least one embodiment according to methods of the present invention, placement pins are used to identify a center point and a midline reference. Before an incision is made, the implant placement device 1300 is placed on a patients shoulder where the K-wire center placement hole 1314 aligns with center point and midline reference aligns with the midline extension 1304 and a midline aperture 1320. Each of the wire guide plugs 1310, 1312 defines a K-wire drill guide hole for locating a point for drilling an anchor hole.

Figure 16:
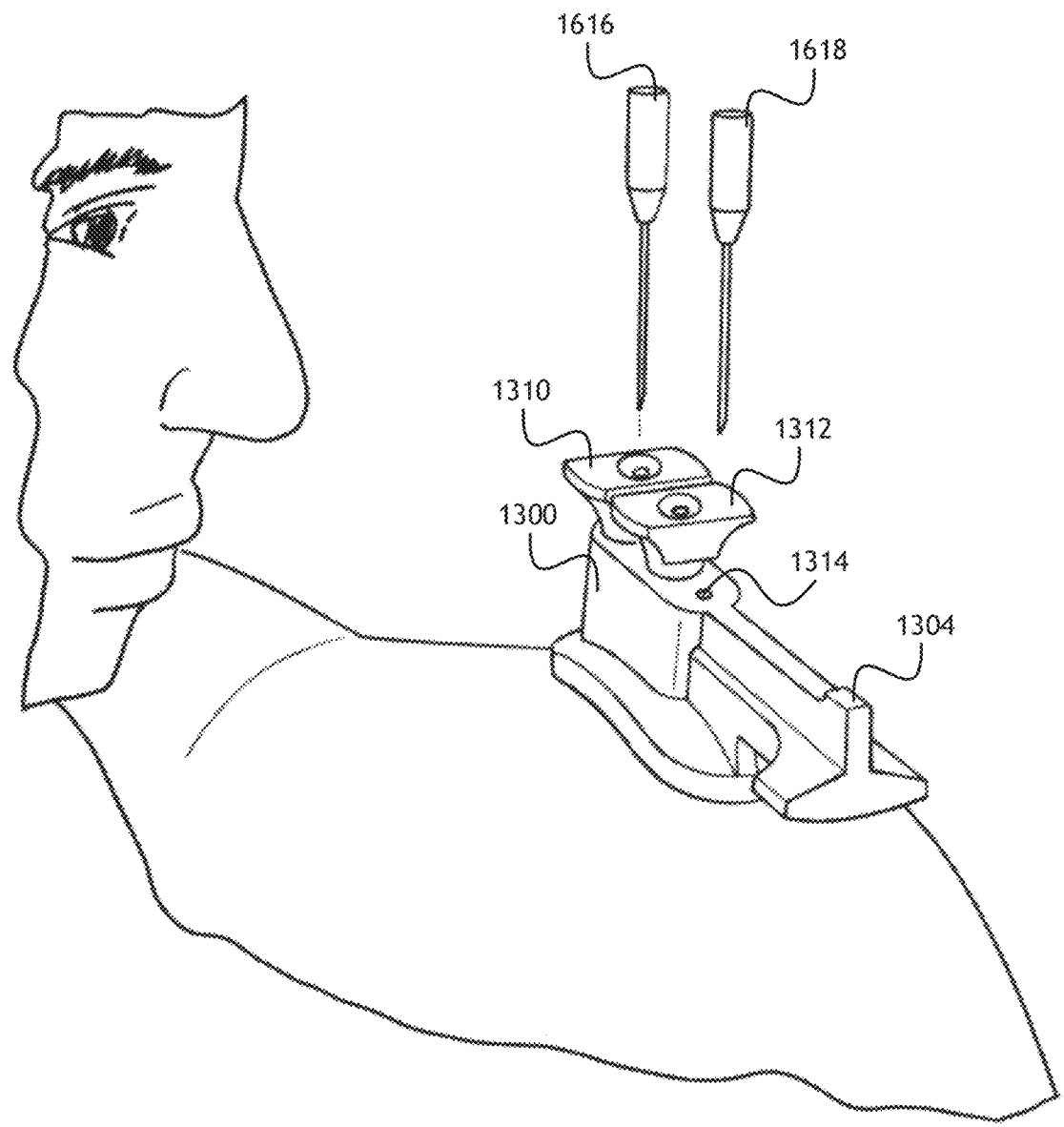
FIG. 16 shows an environmental view of the implant locating device in FIG. 13.

Referring to FIG. 16, an environmental view of the implant locating device in FIG. 13 is shown. Once the implant placement device 1300 is placed on a patients shoulder K-wires 1616, 1618 are inserted into each the wire guide plug 1310, 1312. The implant placement device 1300 can then be removed, leaving the K-wires 1616, 1618 in place. An incision can be made in the patient's skin and the implant placement device 1300 replaced.

Figure 17:
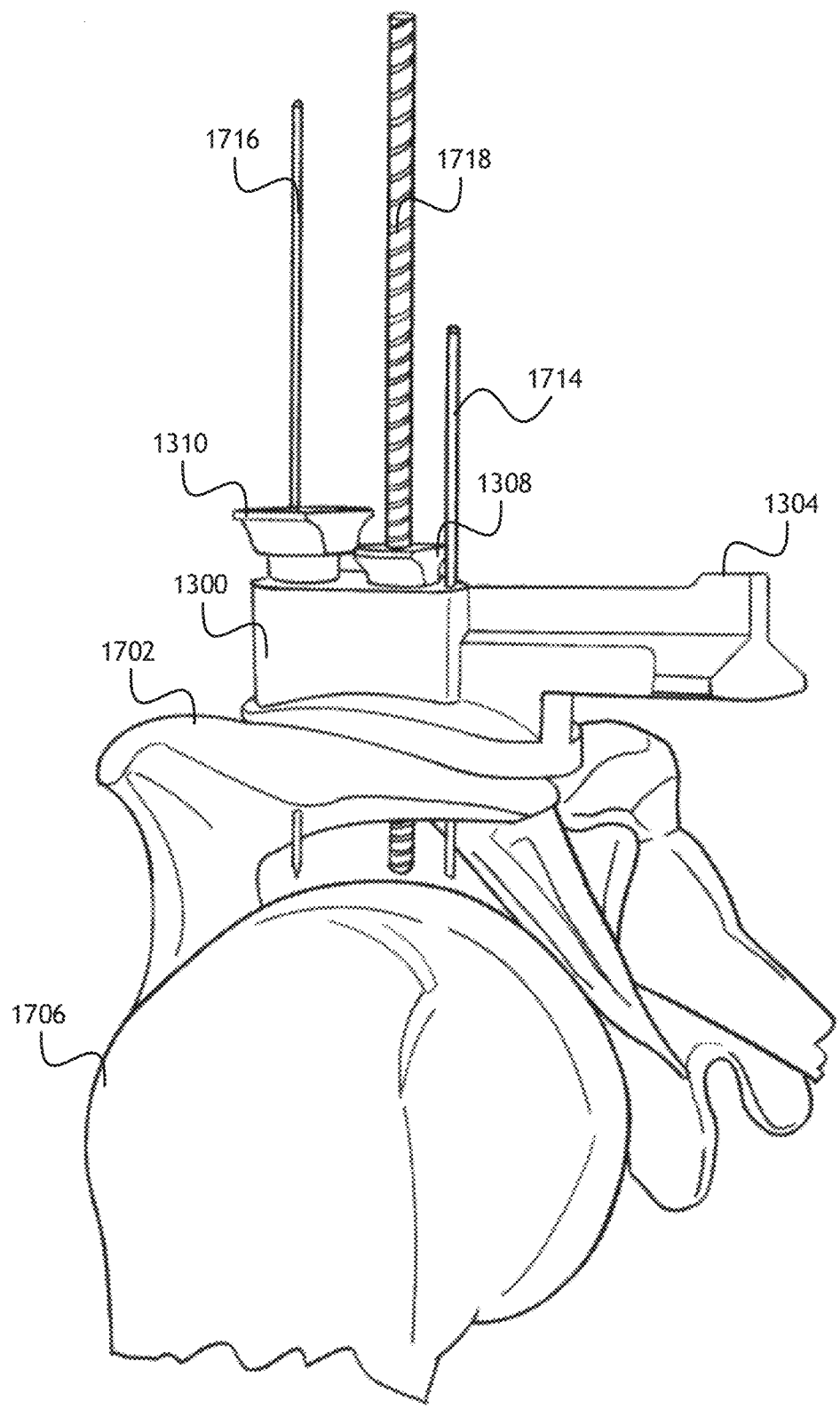
FIG. 17 shows an environmental view of the implant locating device in FIG. 13.

Referring to FIG. 17, an environmental view of the implant locating device in FIG. 13 is shown. After the implant placement device 1300 is placed to abut the soft tissue covering the superior surface of the patient's acromion 1702, with a centering K-wire 1714 in the K-wire center placement hole and K-wires 1716 in the K-wire guide plugs 1310. While the centering K-wire 1714 and at least one K-wire 1716 in a K-wire guide plug 1310 remain in place, one of the K-wire guide plugs is removed (K-wire guide plug 1312 shown removed) leaving a drill guide insert 1308. An appropriate drill bit 1718 is inserted into the drill guide insert 1308 and an anchor hole is drilled. The drill bit 1718 and drill guide insert 1308 are then removed and the drill plug 1316 (not shown) is inserted to hold the implant locating device 1300 stationary with respect to the acromion 1702. The remaining K-wire 1716 and wire guide plug 1310 are then removed and the process is repeated. Two properly located acromion anchor holes are thereby placed in the patient's acromion 1702.

In another embodiment of the present invention, after each anchor hole is drilled, a corresponding drill guide insert 1306, 1308 is removed and a compression sleeve inserted through a hole in the implant placement device 1300. Leaving the implant placement device 1300 in place during insertion of the compression sleeve ensures the proper trajectory of the compression sleeve.

Figure 18:
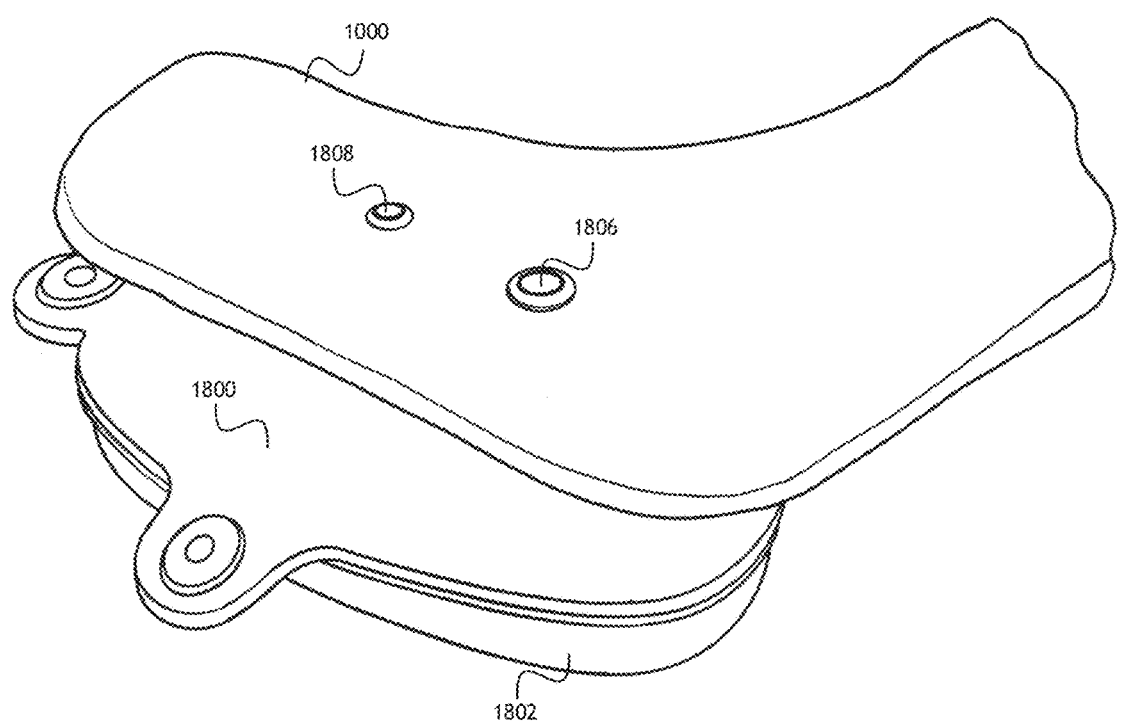
FIG. 18 shows a perspective, environmental view of an implant positioned relative to a patient's acromion.

Referring to FIG. 18, a perspective, environmental view of an implant positioned relative to a patient's acromion is shown. In at least one embodiment, the implant is placed in the acromial arc, inferior to the acromion and CA ligament. In at least one embodiment, an implant including an acromion fixation element 1800 and an inflatable humeral balloon 1802 is implanted in a patient such that the acromion fixation element 1800 abuts an inferior surface of the patient's acromion 1000 (the implant is beneath the acromion 1000). Where the implant includes acromion anchors 1806, 1808 disposed on the acromion fixation element 1800, anchor holes may be drilled in the acromion 1000. In one embodiment, where the location of the implant is determined using a device and method such as described in FIGS. 8, 9, 10, 11 and 12, anchor hole locations are derived from a LAP measurement of the acromion 1000, and the acromion anchors 1806, 1808 are inserted in the anchor holes from the side of the inferior surface. In other embodiments, where the location of the implant is determined using a device and method such as described in FIGS. 13, 15, 16, 17, anchor hole locations are determined directly. The acromion fixation element 1800 may be configured to facilitate tissue ingrowth and thereby facilitate attachment to the inferior surface of the acromion, such as through chemical treatment, surface texturing or other mechanisms.

In at least one embodiment, at least one acromion anchor 1806, 1808 may be configured as a fill valve, or configured to allow access to a fill valve, such that fluid may be added to or removed from a fluid space defined by the acromion fixation element 1800 and the inflatable humeral balloon 1802 after the implant is positioned. For example; after an implant according to the present invention is positioned, a surgeon may pierce a fill valve enabled acromion anchor 1806 with a needle and inject a desired volume of fluid. The surgeon may inject such fluid even through the patient's skin after the implantation surgery is complete.

Figure 19:
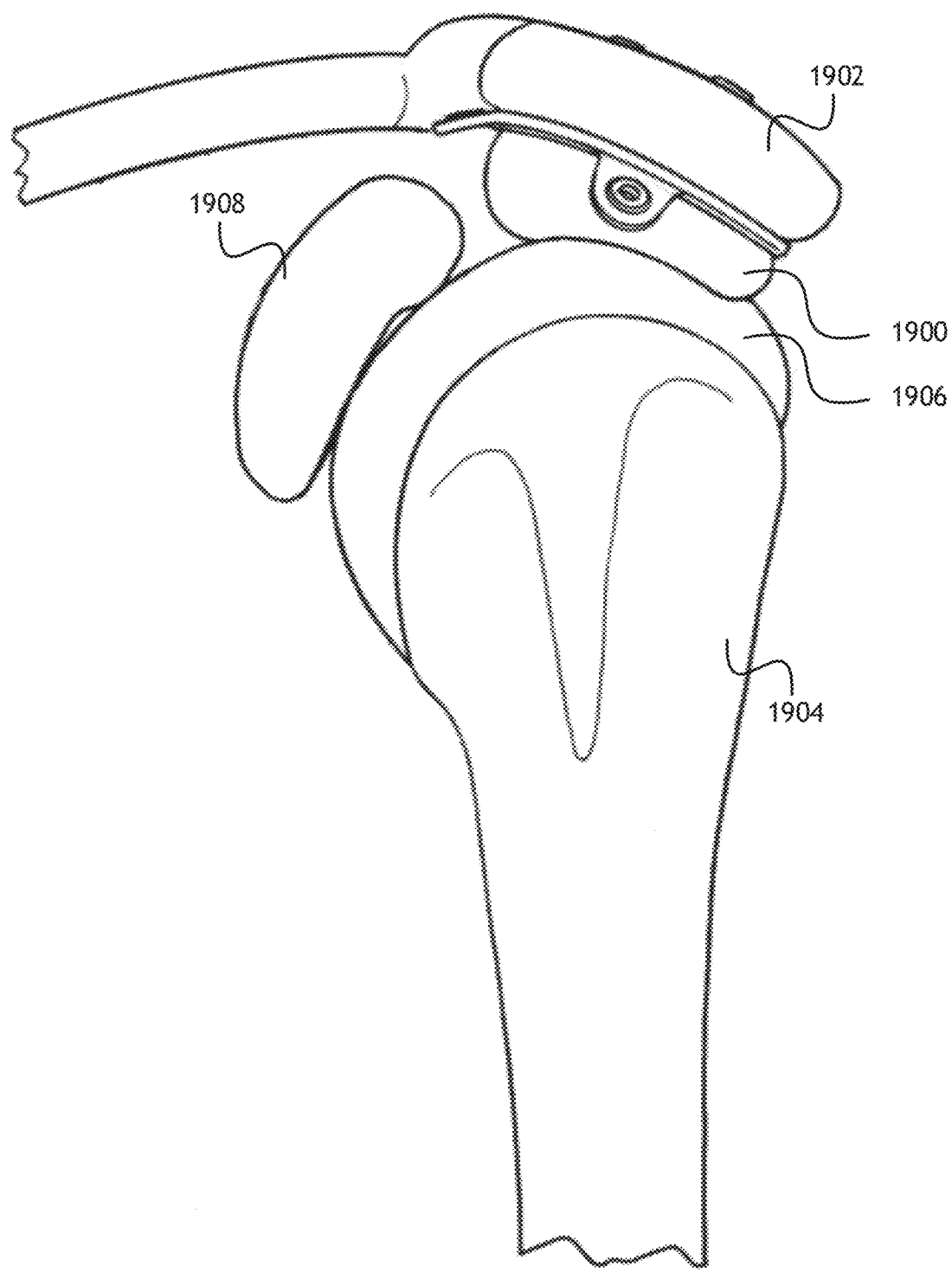
FIG. 19 shows a lateral, environmental view of an implant interposed between a patient's acromion and a corresponding humeral head.
Figure 20:
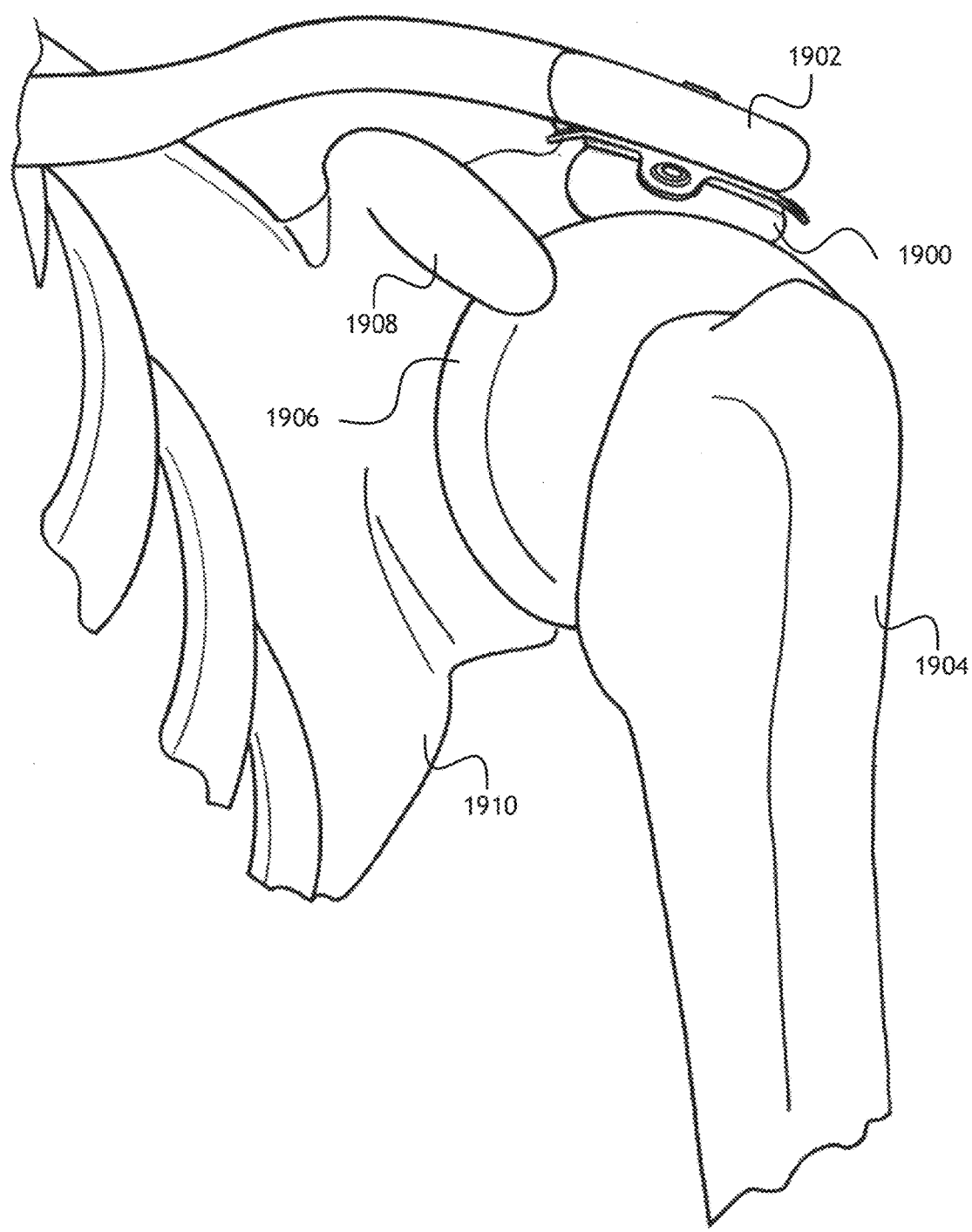
FIG. 20 shows a front, environmental view of an implant interposed between a patient's acromion and a corresponding humeral head.

Referring to FIG. 19 and FIG. 20, a lateral and front respectively, environmental view of an implant interposed between a patient's acromion and a corresponding humeral head are shown. An implant 1900 according to the present invention is interposed between a patient's acromion 1902 and a corresponding humeral head 1906 of the patient's humerus 1904. The implant 1900 may be positioned posterior to the coracoid process 1908 and anterior to the posterior aspect of the acromion 1902. The implant 1900 maintains a desirable separation of the acromion 1902 and humeral head 1906 to prevent painful impingement of anatomical structures in the subacromial space by applying a broad, fluid cushioned force to the humeral head 1906.

A person skilled in the art may appreciate that while embodiments of the present invention described herein specify an implant attached to an acromion to maintain a separation between the acromion and corresponding humeral head; in another embodiment, the implant may be attached to the humeral head such that the implant is stationary with respect to the humeral head.

It is believed that the present invention and many of its attendant advantages will be understood by the foregoing description of embodiments of the present invention, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A method for positioning an implant in a subacromial space comprising:
   identifying a plurality of anatomical landmarks corresponding to locations around the perimeter of an acromion defining an anatomical location of the acromion;
   placing an implant locating device based on the plurality of anatomical landmarks;
   identifying one or more implant anchor locations with the implant locating device;
   making an incision based on at least the one or more implant anchor locations;
   drilling one or more anchor holes, locations of the one or more anchor holes identified by the implant locating device;
   inserting one or more trial implants, each of the one or more trial implants comprising one or more anchor posts, each of the one or more anchor posts configured to engage one of the one or more anchor holes;
   inserting an inflatable implant; and inflating the inflatable implant to a desired volume based on the one or more trial implants.

2. The method of claim 1, further comprising: marking each of the plurality of anatomical landmarks with a placement pin; and locating a implant locating device based on the placement pins.

3. The method of claim 1, further comprising removing bone spurs from an inferior portion of the acromion.

4. The method of claim 1, further comprising inserting an anchor hole collar into each of the two anchor holes.

5. The method of claim 1, further comprising inserting at least one drill guide in the implant locating device.

* * * * *